(12) United States Patent
Takeda et al.

(10) Patent No.: US 11,022,534 B2
(45) Date of Patent: Jun. 1, 2021

(54) GENERATION SOURCE ANALYZING DEVICE AND GENERATION SOURCE ANALYZING SYSTEM

(71) Applicant: FUJI ELECTRIC CO., LTD., Kanagawa (JP)

(72) Inventors: Naoki Takeda, Yokohama (JP); Bo Li, Hachioji (JP); Yoshiki Hasegawa, Hino (JP); Kazuhiro Koizumi, Sagamihara (JP); Yu Kawamura, Hino (JP)

(73) Assignee: FUJI ELECTRIC CO., LTD., Kanagawa (JP)

( * ) Notice: Subject to any disclaimer, the term of this patent is extended or adjusted under 35 U.S.C. 154(b) by 259 days.

(21) Appl. No.: 15/901,899

(22) Filed: Feb. 22, 2018

(65) Prior Publication Data
US 2018/0292302 A1    Oct. 11, 2018

(30) Foreign Application Priority Data

Apr. 6, 2017   (JP) .............................. JP2017-076035

(51) Int. Cl.
*G01N 15/02*     (2006.01)
*G01N 33/00*     (2006.01)
*G01N 15/00*     (2006.01)

(52) U.S. Cl.
CPC ..... *G01N 15/0272* (2013.01); *G01N 33/0032* (2013.01); *G01N 2015/0046* (2013.01)

(58) Field of Classification Search
CPC .................... G01N 15/0272; G01N 33/0032
See application file for complete search history.

(56) References Cited

U.S. PATENT DOCUMENTS

2010/0194574 A1*  8/2010  Monk .................... G01N 21/53
                                                  340/627
2017/0315105 A1* 11/2017  Takeda ............... G01N 33/0036

OTHER PUBLICATIONS

Gary Norris et al. "EPA Positive Matrix Factorization (PMF)5.0 Fundamentals and User Guide", Apr. 2014, EPA pp. 1-124, EPA/600/R-14/108.

* cited by examiner

*Primary Examiner* — Matthew G Marini

(57) ABSTRACT

An analyzing device is provided, which can accurately analyze information related to generation sources. A generation source analyzing device is provided, which includes a measurement value acquiring unit to acquire time-series measurement values of a concentration of each of a plurality of measured object components at a measurement point, a correlation calculating unit to calculate a correlation value between the time-series measurement values of at least one set of the measured object components, and a generation source analyzing unit to analyze information related to generation sources of at least one measured object component based on the correlation value calculated by the correlation calculating unit.

12 Claims, 12 Drawing Sheets

| GENERATION SOURCE | SULFATE | NITRATE | BLACK CARBON | ... |
|---|---|---|---|---|
| SHIP | LARGE | SMALL | LARGE | |
| FUEL OIL BOILER | LARGE | — | LARGE | |
| MOTOR VEHICLE | — | LARGE | LARGE | |
| CONSTRUCTION MACHINE | — | LARGE | LARGE | |
| LARGE-SCALE FIXED SMOKE SOURCE | LARGE | LARGE | — | |
| VOLCANO | LARGE | — | — | |
| DIESEL GENERATOR | — | — | LARGE | |
| ⋮ | | | | |

| TIME | GENERATION SOURCE CANDIDATE |
|---|---|
| ZERO HOURS | GENERATION SOURCE A, GENERATION SOURCE B |
| 1 O'CLOCK | GENERATION SOURCE A, GENERATION SOURCE B |
| 2 O'CLOCK | GENERATION SOURCE A, GENERATION SOURCE B, GENERATION SOURCE C |
| ⋮ | |
| 23 O'CLOCK | GENERATION SOURCE C |
| ZERO HOURS | GENERATION SOURCE A, GENERATION SOURCE B |
| ⋮ | |

| TIME | COMBINATION OF COMPONENTS |
|---|---|
| ZERO HOURS | COMPONENTS a-b |
| 1 O'CLOCK | COMPONENTS a-b |
| 2 O'CLOCK | COMPONENTS a-b, COMPONENTS b-c |
| ⋮ | |
| 23 O'CLOCK | COMPONENTS b-c |
| ZERO HOURS | COMPONENTS a-b |
| ⋮ | |

| GENERATION SOURCE | SULFATE | NITRATE | BLACK CARBON | ... | LOCATION INFORMATION |
|---|---|---|---|---|---|
| SHIP | LARGE | SMALL | LARGE | | |
| FUEL OIL BOILER | LARGE | — | LARGE | | N2, E2 |
| MOTOR VEHICLE | — | LARGE | LARGE | | |
| CONSTRUCTION MACHINE | — | LARGE | LARGE | | |
| LARGE-SCALE FIXED SMOKE SOURCE | LARGE | LARGE | — | | N5, E5 |
| VOLCANO | LARGE | — | — | | N6, E6 |
| DIESEL GENERATOR | — | — | LARGE | | N7, E8 |
| ⋮ | | | | | |

GENERATION SOURCE ANALYZING DEVICE AND GENERATION SOURCE ANALYZING SYSTEM

The contents of the following Japanese patent application are incorporated herein by reference:

NO. 2017-076035 filed in JP on Apr. 6, 2017.

BACKGROUND

1. Technical Field

The present invention relates to a generation source analyzing device and a generation source analyzing system.

2. Related Art

Conventionally, a method of analyzing, by using a receptor model, whether an object substance such as a fine particulate matter (PM 2.5) in the atmosphere is generated from any of generation sources has been known (for example, refer to Non-Patent Document 1).

[Non-Patent Document 1] "Positive Matrix Factorization (PMF) 5.0 Fundamentals and User Guide", April, 2014, EPA

SUMMARY

With the analyzing method using the conventional receptor model, a sufficient analysis becomes impossible to be performed if a number of candidates of the generation sources becomes more than a number of measured component items measured at a certain measurement point at a certain measurement time. Specifically, in the conventional analyzing method, an expression for each component is created based on an assumption that the concentration of each of the measured components at a certain measurement point at a certain measurement time is a sum of values obtained by respectively multiplying the concentration of the component emitted by each of the generation sources by a degree of contribution of the generation source emitting the component. Then, the simultaneous equation is solved, where the degree of contribution of the generation source is set as an unknown number. However, if the number of candidates of the generation sources (that is, the unknown number) is more than a number of types of the components that can be measured, it becomes impossible to solve the simultaneous equation. For this reason, a method of analyzing the generation sources at a different viewpoint from that of the conventional analyzing method has been desired.

In a first aspect of the present invention, a generation source analyzing device is provided, which analyzes information related to generation sources. The generation source analyzing device may include a measurement value acquiring unit to acquire time-series measurement values of a concentration of each of a plurality of measured object components at a measurement point. The generation source analyzing device may include a correlation calculating unit to calculate a correlation value between the time-series measurement values of at least one set of the measured object components. The generation source analyzing device may include a generation source analyzing unit to analyze information related to generation sources of the at least one measured object component based on the correlation value calculated by the correlation calculating unit.

The generation source analyzing unit may extract candidates of the generation sources that emitted the at least one measured object component. The generation source analyzing device may include a generation source database that has recorded an emitted measured object component profile of each of a plurality of generation sources. The generation source analyzing unit may extract, from the generation source database as the candidates of the generation sources, generation sources that emit at the same time a set of measured object components having a correlation value that exceeds a reference correlation value. The generation source database may further record information indicating a distance between each of the generation sources and the measurement point.

The generation source analyzing unit may calculate a contribution proportion of each extracted candidate of the generation sources relative to the measurement value. The generation source analyzing unit may extract the candidates of the generation sources further based on an individual measurement value of each measured object component. The generation source analyzing unit may perform a primary extraction of the candidates of the generation sources based on the individual measurement value of each measured object component, and perform a secondary extraction of the candidates of the generation sources from the candidates obtained by the primary extraction based on the correlation value calculated by the correlation calculating unit.

The generation source analyzing unit may extract the candidates of the generation sources further based on a length of a period in which the correlation value exceeds the reference correlation value. The correlation calculating unit may extract the candidates of the generation sources based on a variation of the correlation value. The generation source analyzing unit may extract the candidates of the generation sources further based on weather data.

The generation source analyzing unit may analyze, based on the correlation value, a combination of two or more measured object components emitted at the same time from any of the generation sources. The correlation calculating unit may extract the variation component, which is equal to or higher than a predetermined frequency, of the time-series measurement values of each of the measured object components to calculate the correlation value.

In a second aspect of the present invention, a generation source analyzing system is provided, which includes the generation source analyzing device according to the first aspect, and one or more measuring devices to measure a concentration of each of a plurality of measured object components at a measurement point. The generation source analyzing device and each of the measuring devices may be connected to each other via a communication network.

The summary clause does not necessarily describe all necessary features of the embodiments of the present invention. The present invention may also be a sub-combination of the features described above.

BRIEF DESCRIPTION OF THE DRAWINGS

FIG. 3 is a drawing showing one example of generation source profiles stored by a generation source database 40.

FIG. 4 is a drawing showing one example of information presented by a displaying unit 50.

FIG. 5 is a drawing showing another example of the information presented by the displaying unit 50.

FIG. 6 is a flowchart showing one example of a process of generating a generation source profile corrected according to the distance and the like.

FIG. 7 is a drawing showing another example of the generation source profile recorded by the generation source database 40.

DESCRIPTION OF EXEMPLARY EMBODIMENTS

Hereinafter, some embodiments of the present invention will be described. The embodiments do not limit the invention according to the claims, and all the combinations of the features described in the embodiments are not necessarily essential to means provided by aspects of the invention.

Figure 1:
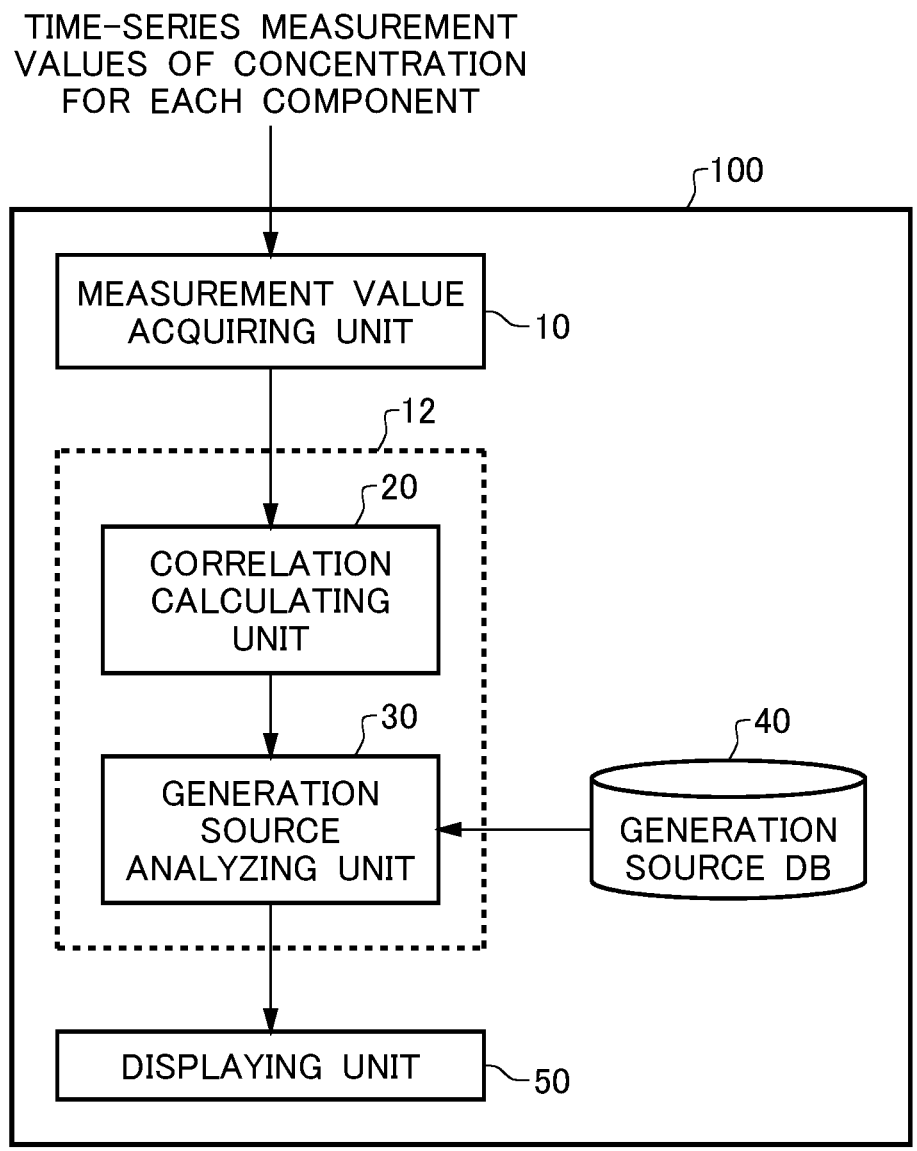
FIG. 1 is a block diagram showing one example of a generation source analyzing device 100 according to one embodiment of the present invention.

FIG. 1 is a block diagram showing one example of the generation source analyzing device 100 according to one embodiment of the present invention. The generation source analyzing device 100 analyzes, based on a concentration of each of a plurality of measured object components at a predetermined measurement point, information related to generation sources of the measured object components. The measured object component refers to a fine particulate matter, for example, a sulfate, a nitrate, a black carbon, and the like. Also, a concentration of the measured object component refers to a mass concentration ($g/m^3$), for example. In the present specification, the mass concentration may be simply referred to as a concentration. The generation source refers to an equipment to emit a fine particulate matter or precursor gas which is a source of the fine particulate matter, for example, a factory, a power plant, a motor vehicle, and the like.

The generation source analyzing device 100 includes a measurement value acquiring unit 10 and an information processing unit 12. The information processing unit 12 includes a correlation calculating unit 20 and a generation source analyzing unit 30. The information processing unit 12 may be a computer having an arithmetic device such as a CPU and the like, and a memory. The arithmetic device may operate according to a program stored in the memory and serve as the correlation calculating unit 20 and the generation source analyzing unit 30. The computer may have a memory that stores arithmetic results and the like obtained in the arithmetic device.

The measurement value acquiring unit 10 acquires the time-series measurement values of the concentration of each of the plurality of measured object components at the measurement point. The measurement value acquiring unit 10 may acquires the measurement value measured by an external measuring device. Also, the measurement value acquiring unit 10 may measure the concentration of each of the measured object components.

The time-series measurement values refer to measurement values measured at different timings at least twice. The measurement timing may be a fixed interval, or may be an unfixed interval. As one example, the measurement value acquiring unit 10 acquires the measurement value measured at a time interval which is equal to or less than one hour. The measurement timing for each measured object component may be the same, or may be different from each other. Also, the measurement interval for each measured object component may be the same, or may be different from each other.

The correlation calculating unit 20 calculates a correlation value between the time-series measurement values of at least one set of the measured object components. The correlation calculating unit 20 of the present example calculates the correlation values respectively between the measurement values of all combinations of the plurality of measured object components. The combinations include not only a combination of two measured object components but also a combination of three or more measured object components. For example, in a case where the measured object components of which the measurement values are acquired by the measurement value acquiring unit 10 are three components a, b, and c, the correlation calculating unit 20 calculates four kinds of correlation values: a correlation value (a, b), a correlation value (a, c), a correlation value (b, c), and a correlation value (a, b, c). In the present specification, the correlation value (x, y) is set as the correlation value between the measurement value of the component x and the measurement value of the component y. Also, in the present specification, the measured object component may be simply referred to as a component.

The generation source analyzing unit 30 analyzes information related to the generation sources of at least one measured object component based on the correlation value calculated by the correlation calculating unit 20. The generation source analyzing unit 30 of the present example extracts the candidates of the generation sources that emitted the at least one measured object component. The generation source analyzing unit 30 may extract a plurality of candidates of the generation sources.

The generation source analyzing device 100 of the present example further includes a generation source database 40. The generation source database 40 records an emitted measured object component profile of each of the plurality of generation sources. The measured object component profile includes information about the types of the measured object components emitted by each generation source. For example, the generation source database 40 records the profile indicating whether each of the plurality of generation sources emits any of the plurality of measured object components.

The generation source analyzing unit 30 extracts, from the generation source database as the candidates of the generation sources, the generation sources which emit at the same time all measured object components included in the set of measured object components having the correlation value which exceeds the reference correlation value. For example, if the correlation value between the components a and b exceeds the reference correlation value, the generation source analyzing unit 30 extracts the generation sources which emit at the same time the components a and b as the candidates of the generation sources of the components a and b.

In this way, the extraction of the candidates of the generation sources can be performed by using the correlation value between the measurement values. Also, because the correlation values can be calculated by respectively combining the measured object components, more kinds of the correlation values than a number of types of the measured object components can be calculated. For this reason, the extraction of the candidates of the generation sources can be performed more appropriately.

For example, if the measured object components are the three components a, b, and c, according to the above-described four kinds of correlation values, various patterns can be detected, such as a case where all of the components a, b, and c are correlated with each other and varied, a case where only the components a and b are correlated with each other and varied, a case where only the components a and c are correlated with each other and varied, a case where only the components b and c are correlated with each other and varied, and a case where all of the components are not correlated with one another. The generation source analyzing unit 30 extracts the generation sources which match with these patterns based on the profiles stored in the generation source database 40. The generation source analyzing unit 30 may extract the candidates of the generation sources for each measured object component.

The generation source analyzing device 100 of the present example further includes a displaying unit 50. The displaying unit 50 displays the candidates of the generation sources extracted by the generation source analyzing unit 30. The displaying unit 50 may display the candidates of the generation sources for each measured object component.

Figure 2:
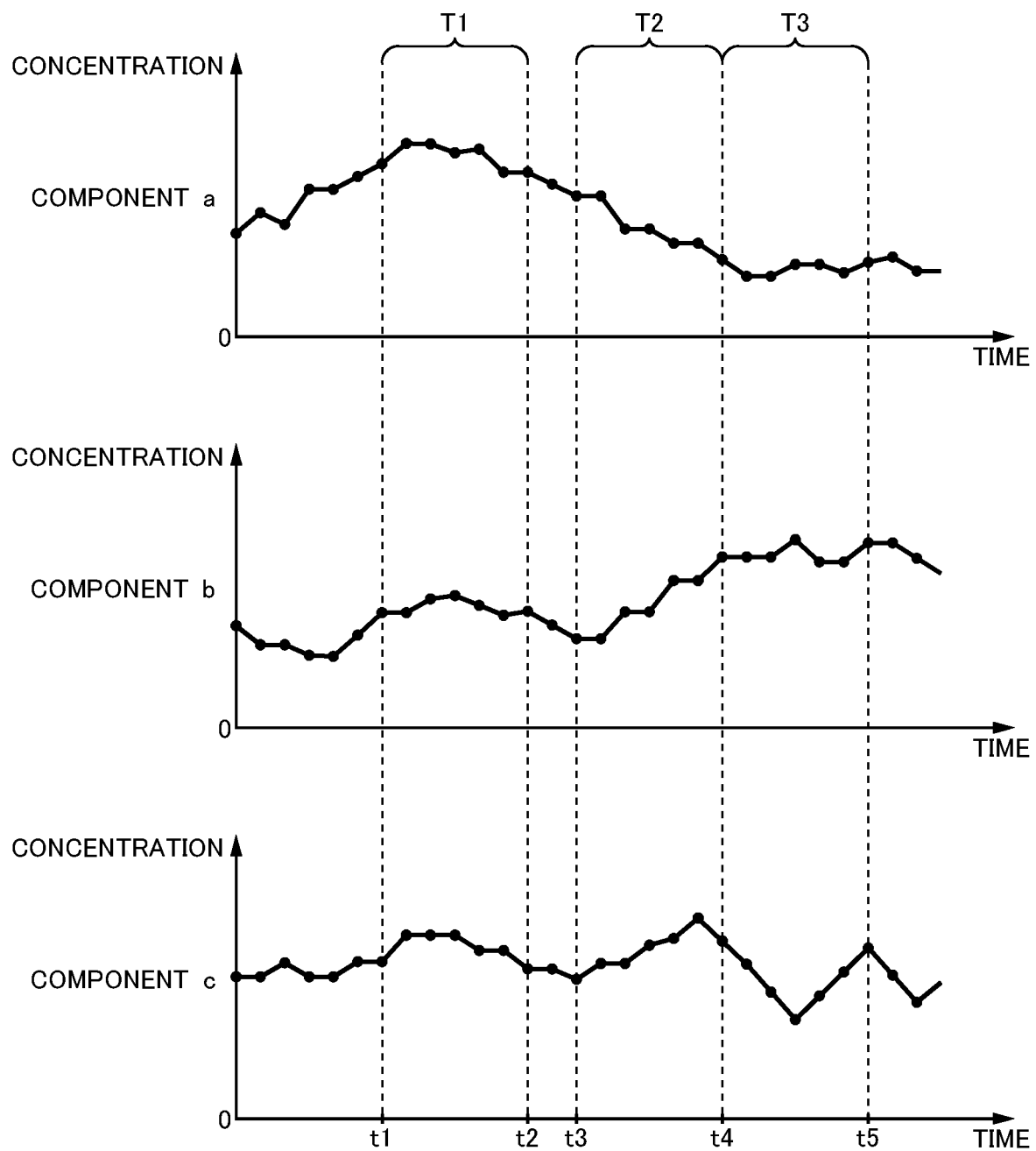
FIG. 2 is a drawing showing one example of time-series concentration measurement values of each measured object component.

FIG. 2 is a drawing showing one example of time-series concentration measurement values of each measured object component. In FIG. 2, the horizontal axis represents the measurement time and the vertical axis represents the measured mass concentration. In the example of FIG. 2, the concentration measurement values of the three components a, b, and c are shown.

The correlation calculating unit 20 calculates the correlation values relative to data in a predetermined time range. The time-series correlation values can be calculated by shifting the time range in a time direction by one time unit and calculating the correlation value at each time position. A central time in the time range may be set as the time corresponding to the correlation value. The time range is approximately one day, for example. The measured object substance is often emitted due to human activities, and a cycle of the concentration variation is often set as one day unit. For this reason, the correlation of the concentration variation can be appropriately determined by setting the time range to one day.

The correlation value r between the two components a and b is calculated according to the following expression, for example.

$$r = \frac{\sum_{i=1}^{n}(a_i - \bar{a})(b_i - \bar{b})}{\left(\left(\sum_{i=1}^{n}(a_i - \bar{a})^2\right)\left(\sum_{i=1}^{n}(b_i - \bar{b})^2\right)\right)^{\frac{1}{2}}}$$

[Expression 1]

It should be noted that the concentration of the component a at a time i is set as $a_i$ and an arithmetic mean of the concentration $a_i$ is shown by a symbol a with a bar added thereover, and the concentration of the component b at the time i is set as $b_i$ and an arithmetic mean of the concentration $b_i$ is shown by a symbol b with a bar added thereover. Also, n corresponds to a length of the time range.

In the example shown in FIG. 2, the components a, b, and c are showing similar variation patterns during a period T1. For this reason, during the period T1, the correlation value (a, b, c) becomes high and exceeds the reference correlation value. In this case, the generation source analyzing unit 30 extracts the generation sources which emit at the same time the components a, b, and c as the candidates of the generation sources during the period T1. During the period T1, if the correlation value (a, b), the correlation value (a, c), and the correlation value (b, c) also become high and exceed the reference correlation value, the generation source analyzing unit 30 may extract, as the candidates, the generation sources which emit at the same time the components a and b, the generation sources which emit at the same time the components a and c, and the generation sources which emit at the same time the components b and c.

Also, during a period T2, the components b and c are showing similar variation patterns. Also, the component a is showing a different variation pattern from those of the components b and c. For this reason, during the period T2, the correlation value (b, c) becomes high and exceeds the reference correlation value. Also, the correlation value (a, b) and the correlation value (a, c) do not exceed the reference correlation value. In this case, the generation source analyzing unit 30 extracts, as the candidates, the generation sources that emit at the same time the components b and c and that do not emit the component a. The generation source analyzing unit 30 may extract, as the candidates, the generation sources that emit the component a and that do not emit the components b and c. That is, if a component, which has correlation values respectively between the component and all of the other components less than the reference correlation value, is present, the generation sources which only emit the component may be extracted as the candidates.

Also, during a period T3, the components a, b, and c respectively are showing different variation patterns. For this reason, during the period T3, all of the correlation values do not exceed the reference correlation value. In this case, the generation source analyzing unit 30 extracts, as the candidates, the generation sources which respectively independently emit the components a, b, and c.

In this way, the candidates of the generation sources can be extracted based on the correlation values between the respectively measured object components. Although the example of FIG. 2 has shown the example that there are three types of the measured object components, there may be two types of, or there may be four or more of the measured object components.

It should be noted that the correlation calculating unit 20 may extract the variation component, which is equal to or higher than a predetermined frequency, of the time-series measurement values of each of the measured object components to calculate the correlation value therebetween. Generally, the measurement value of each of the measured object components includes a fixed base component and a variation component that is varied relative to the time.

As a result of the contribution of numerous generation sources present over a very wide range relative to the measurement point, it can be estimated that a fixed base component is generally generated. For this reason, it is relatively difficult to specify the contribution of a specified generation source from the base component. The extraction of the candidates of the generation sources can by more accurately performed by removing the base component and calculating the correlation values based on the variation component.

FIG. 3 is a drawing showing one example of the generation source profile stored by the generation source database 40. The generation source database 40 stores whether the measured object components, such as the sulfate and the nitrate, are emitted or not in association with each generation source such as a ship and a fuel oil boiler. The generation source database 40 may further store information indicating an emission amount of each of the measured object components. In FIG. 3, the emission amount of each of the measured object components is respectively shown by three levels, i. e., 0 (–), small, and large. It should be noted that even if the emission amount is not exactly 0 g, in a case where the emission amount is equal to or less than a predetermined value, the emission amount may be set as the emission amount 0.

The generation source analyzing unit 30 of the present example extracts the candidates of the generation sources of each of the measured object components based on the correlation value calculated by the correlation calculating unit 20 and the generation source profile stored by the generation source database 40.

For example, if the correlation value between the sulfate and the nitrate is higher than the reference correlation value and the correlation value between the black carbon and another component is lower than the reference correlation value, the generation source analyzing unit 30 extracts, as the candidate of the generation sources of the sulfate and the nitrate, a large-scale fixed smoke source that emits at the same time the sulfate and the nitrate and that does not emit the black carbon at the same time. The large-scale fixed smoke source is a factory, for example.

If the correlation value between predetermined components is higher than the reference correlation value, the generation source analyzing unit 30 may extract a plurality of candidates of the generation sources corresponding to the components. For example, if the correlation value between the nitrate and the black carbon is higher than the reference correlation value and the correlation value between other components is lower than the reference correlation value, the generation source analyzing unit 30 extracts a motor vehicle and a construction machine as the candidates of the generation sources.

FIG. 4 is a drawing showing one example of information presented by the displaying unit 50. The generation source analyzing unit 30 of the present example extracts the candidates of the generation sources at a predetermined measurement point at each predetermined time interval. The displaying unit 50 displays the candidates of the generation sources extracted by the generation source analyzing unit 30 in a time series. The displaying unit 50 may display the candidates of the generation sources for each measured object component.

The generation source analyzing unit 30 may further calculate a probability that the candidate is the generation source of the component for each of the extracted candidates. The generation source analyzing unit 30 may calculate the probability based on the emission amount of each component in the generation sources. For example, if there are a plurality of generation sources which are emitting a combination of the components that have the correlation value higher than the reference correlation value, the generation source analyzing unit 30 may set the probability of the generation sources having a larger emission amount to a higher one. It is preferable to correct the emission amount of each component in the generation source according to information indicating the distance from the measurement point to the generation source. For example, as the distance is larger, the emission amount of each component in the generation source is corrected to a small one.

FIG. 5 is a drawing showing another example of the information presented by the displaying unit 50. The generation source analyzing unit 30 of the present example analyzes, based on the correlation values, the combinations of two or more measured object components which are estimated to have been emitted at the same time from any of the generation sources. For example, if the correlation value between the sulfate and the nitrate exceeds the reference correlation value at a certain time, the generation source analyzing unit 30 determines that the generation source exists which simultaneously emits the sulfate and the nitrate at the time.

The generation source analyzing unit 30 presents the combinations of the measured object components estimated to have been emitted at the same time in one or more generation sources at each predetermined time interval. The displaying unit 50 displays the combinations of the measured object components extracted by the generation source analyzing unit 30 in a time series.

The generation source analyzing unit 30 may further calculate the probability that the corresponding generation source exists to the combinations of the extracted measured object components. For example, the generation source analyzing unit 30 may calculate the probability that the corresponding generation source exists higher as the correlation value between the components is higher. Also, as the correlation value between the components is higher, the generation source analyzing unit 30 may calculate the probability that the generation source in a close distance from the measurement point exists high.

Figure 6:
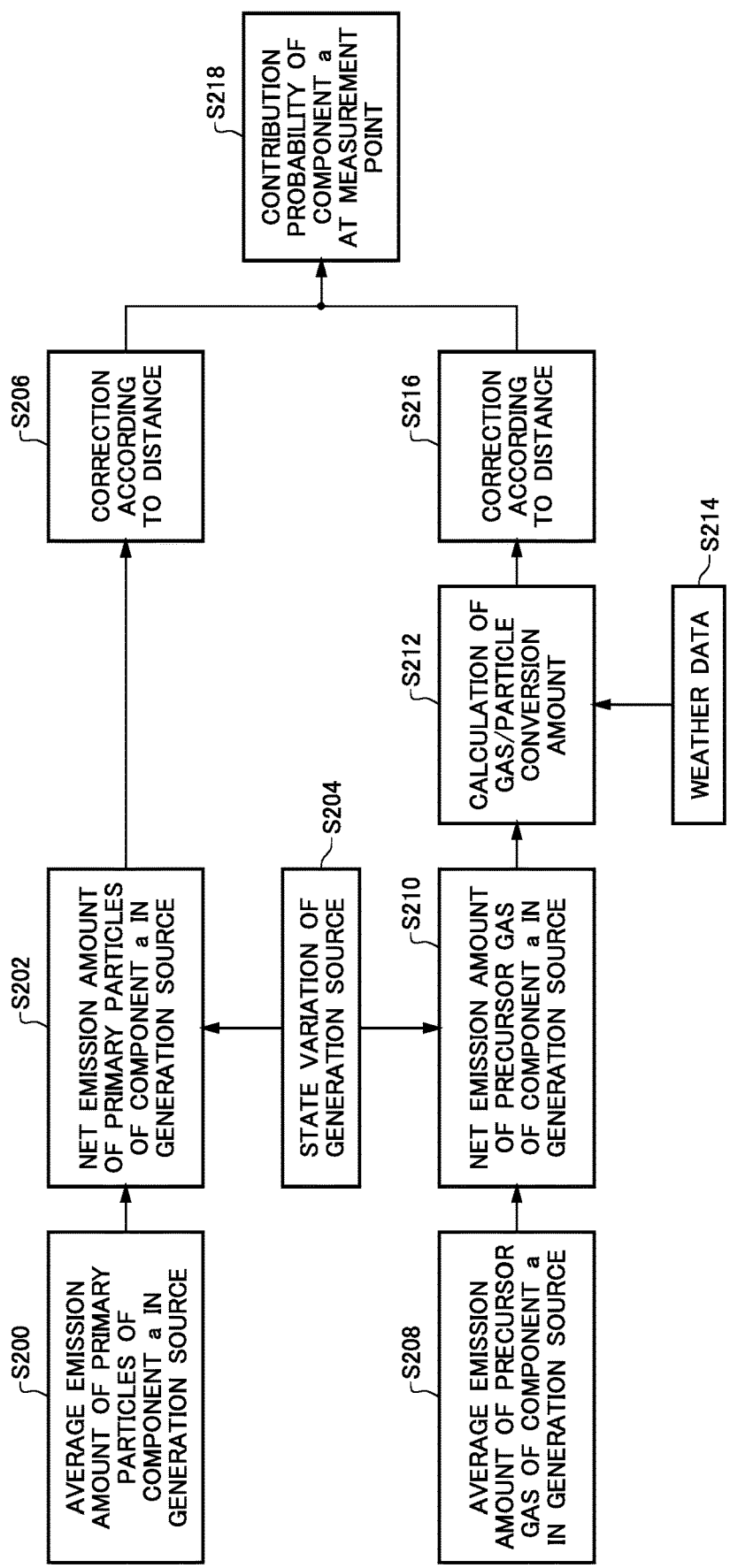

FIG. 6 is a flowchart showing one example of the process of generating the generation source profiles corrected according to the distance and the like. The information processing unit 12 may perform the process. Although the process for the component a is described in FIG. 6, processes for other components are also similar. The information processing unit 12 acquires an average emission amount of primary particles of the component a in each of the generation sources (S200). The primary particles refer to those being emitted in a particle state from the generation source. The average emission amount refers to an average emission amount in a predetermined period such as one day unit, for example.

Also, the information processing unit 12 acquires the average emission amount of the precursor gas of the component a in each of the generation sources (S208). The precursor gas is the gas that is emitted in a gas state from the generation source and that may be converted into particles of the component a in the atmosphere.

The information processing unit 12 acquires the information related to a state variation of the generation source (S204). The information related to the state variation of the generation source refers to the information that exercises an influence on the emission amounts of the primary particles and the precursor gas of the component a from the generation source, such as the information indicating an operation state of a factory in a time series, for example. The information processing unit 12 calculates a net emission amount of the primary particles of the component a at each time based on the information of the average emission amount of the primary particles of the component a and the information of the state variation of the generation source (S202). Also, the information processing unit 12 calculates a net emission amount of the precursor gas of the component a at each time based on the information of the average emission amount of the precursor gas of the component a and the information of the state variation of the generation source (S210).

The information processing unit 12 calculates an amount of the particles converted from the precursor gas based on the net emission amount of the precursor gas of the component a (S212). The information processing unit 12 may acquire the information that exercises an influence on a conversion rate from the gas to the particles, such as weather data (S214). The information processing unit 12 may calculate the converted particle amount further based on the information. For example, the weather data includes a temperature of a region, an amount of rainfall, a wind speed, and the like.

The information processing unit 12 corrects the net emission amount of the primary particles of the component a according to the distance from the generation source to the measurement point to calculate the primary particle amount of the component a reaching the measurement point (S206). The information processing unit 12 may use a correction factor by which the primary particle amount of the component a reaching the measurement point becomes small as the distance is larger.

The information processing unit 12 corrects the particle amount converted from the precursor gas according to the distance between the generation source and the measurement point to calculate the particle amount resulted from the precursor gas reaching the measurement point (S216). The information processing unit 12 may use a correction factor by which the amount of the particles of the component a reaching the measurement point becomes small as the distance is larger. The correction factor used at S216 may be the same as or may be different from the correction factor used at S206. Considering that the primary particles reach a distant place easily compared to the precursor gas, the correction factor at S216 may have an attenuation rate of the particle amount relative to the distance larger than that of the correction factor at S206.

The information processing unit 12 calculates a sum of the primary particle amount calculated at S206 and the particle amount calculated at S216 (S218). The particle amount calculated at S218 corresponds to the probability that the component a emitted from the generation source contributes to the concentration of the component a at the measurement point. The information processing unit 12 may use the particle amount calculated at S218 as the emission amount of each component shown in FIG. 3.

FIG. 7 is a drawing showing another example of the generation source profiles recorded by the generation source database 40. The generation source database 40 of the present example records the information indicating the distance between each of the generation sources and the measurement point. The information in the present example is the location information of each of the generation sources. The location information may be information indicating the longitude and the latitude, or may be other information. In a case where numerous individual pieces are the generation sources, such as motor vehicles, the location information of the generation source may not have been registered. In this case, the distance information between the measurement point and the generation source may use a preset reference value for each type of the generation sources. The reference value of the distance may be 0.

The measurement value acquiring unit 10 of the present example acquires the location information of the measurement point together with the measurement value of the concentration of each component. The generation source analyzing unit 30 may calculate the distance between the measurement point and the generation source based on the location information of the measurement point and the location information of each of the generation sources. The generation source analyzing unit 30 may use the calculated distance information in the processes at S206 and S216 shown in FIG. 6. According to such a configuration, the generation source analyzing device 100 can create the generation source profile considering the distance between the measurement point and each generation source to extract the candidates of the generation sources.

Figure 8:
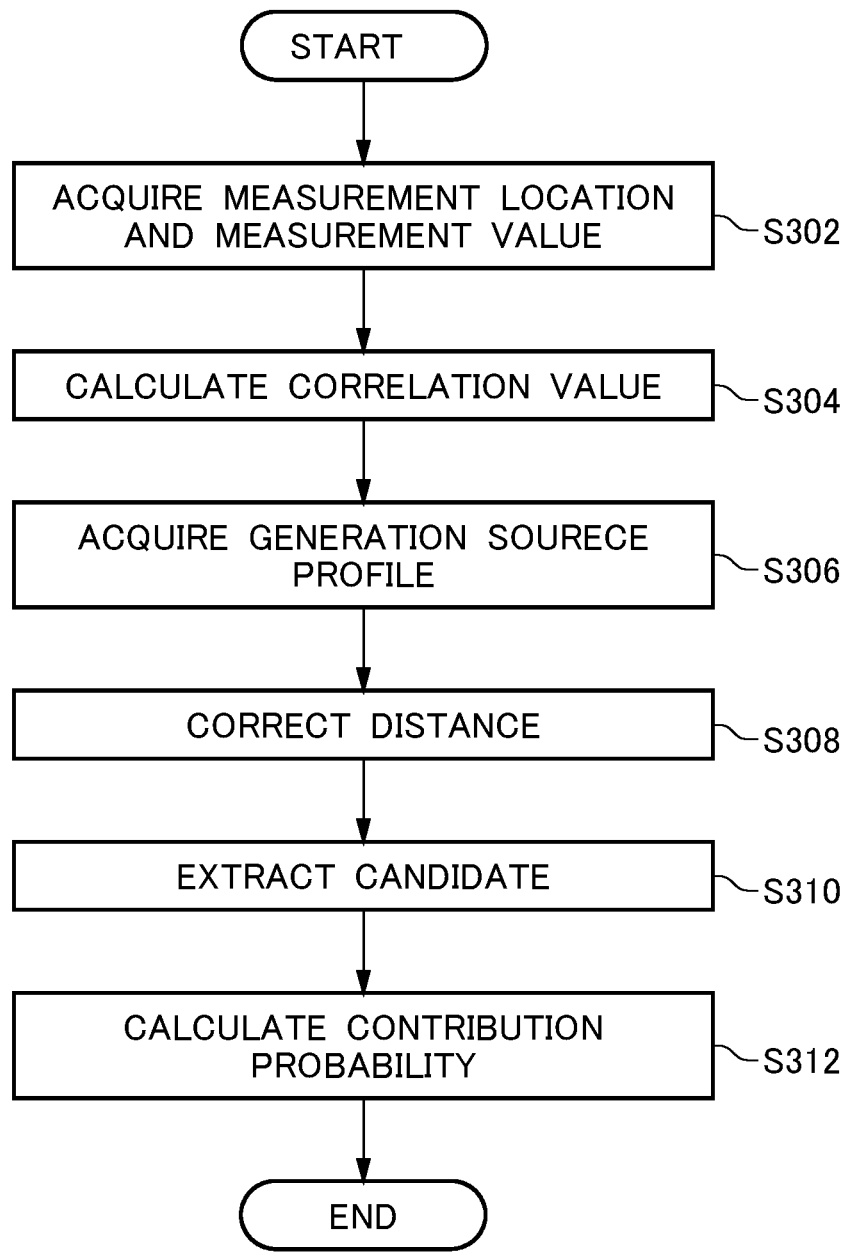
FIG. 8 is a flowchart showing an operation example of the generation source analyzing device 100.

FIG. 8 is a flowchart showing an operation example of the generation source analyzing device 100. The measurement value acquiring unit 10 acquires the measurement value of each measured object component at a predetermined measurement point and the location information about the measurement point (S302). Next, the correlation calculating unit 20 calculates the correlation value for each combination of the measured object components (S304).

Next, the generation source analyzing unit 30 acquires the generation source profiles from the generation source database 40 (S306). The generation source profiles may include the emission amounts of the primary particles and the precursor gas of each component in each generation source, the location information of each generation source, the information indicating the state variation of each generation source, and the like.

The generation source analyzing unit 30 corrects the emission amount of each component in each generation source according to the processing method shown in FIG. 6 (S308). The generation source analyzing unit 30 extracts the candidates of the generation sources which emitted each component measured at the measurement point based on the corrected emission amount of each component (S310). For example, if the correlation value between the measurement values of the components a and b exceeds the reference correlation value, the generation source analyzing unit 30 extracts, as the candidates, the generation sources in which both of the emission amounts of the components a and b corrected according to the distance and the like are equal to or greater than the reference value.

It should be noted that the generation source analyzing unit 30 may extract the candidates of the generation sources further based on the individual measurement value of each of the measured object components. For example, if the individual measurement value of any of the measured object components falls below the predetermined reference concentration value, the generation source in which the emission amount of the component is equal to or greater than the predetermined reference emission value is excluded from the candidates. It is preferable that the emission amount of the component has been corrected according to the distance between the measurement point and each generation source, as the example shown in FIG. 6.

For example, if the measurement value of the component a falls below the predetermined reference concentration value, the generation source analyzing unit 30 excludes, from the candidates, the generation sources in which the emission amount of the component a corrected according to the distance is equal to or greater than the predetermined reference emission value. As one example, if the measurement value of the component a is approximately zero, the generation source analyzing unit 30 excludes the generation source in which the emission amount of the component a corrected according to the distance and the like is equal to or greater than the predetermined reference emission value.

The generation source analyzing unit 30 may perform a primary extraction of the candidates of the generation sources based on the individual measurement value of each of the measured object components. The primary extraction may be a process of excluding the predetermined generation sources from the candidates, as described above. The generation source analyzing unit 30 performs a secondary extraction of the candidates of the generation sources based on the correlation value calculated by the correlation calculating unit 20 from the candidates obtained by the primary extraction. According to such a process, the candidates of the generation sources can be more accurately extracted.

The generation source analyzing unit 30 calculates the contribution proportion of each of the extracted candidates of the generation sources relative to the concentration of fine particles measured at the measurement point (S312). For example, as the generation source has a larger emission amount corrected according to the distance and the like, the generation source analyzing unit 30 may calculate the contribution proportion of the generation source relative to the measurement point large. At S312, the contribution proportion of the extracted candidates of the generation sources may be calculated by using a publicly known method such as CMB (Chemical Mass Balance) method or PMF (Positive Matrix Factorization) method.

According to such a process, the candidates of the generation sources can be extracted based on the correlation value between the measurement values of each of the components. Also, considering the distance between the generation source and the measurement point, and the like, the candidates of the generation sources can be extracted and the contribution proportion can be calculated as well.

Figure 9:
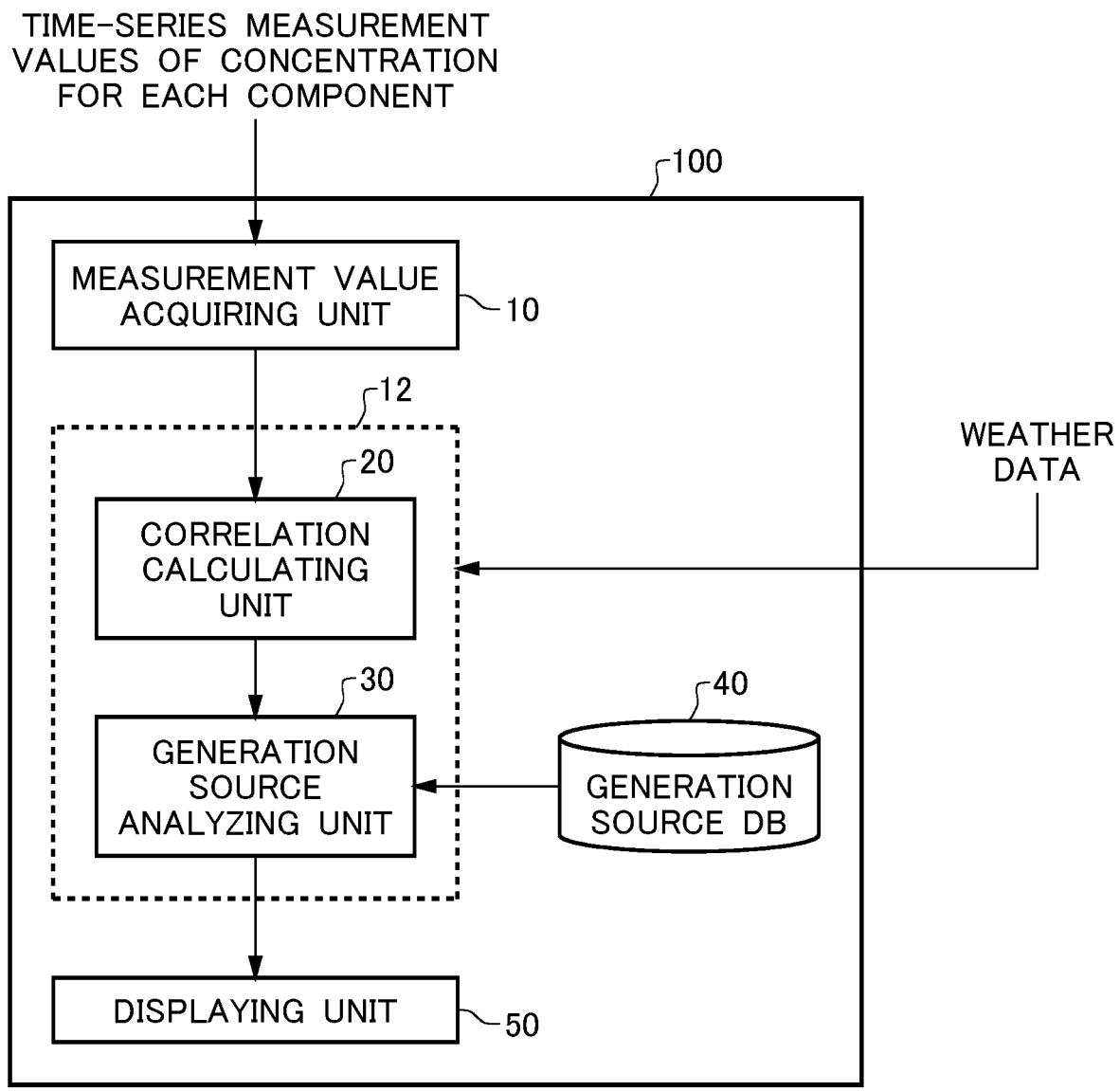
FIG. 9 is a drawing showing another configuration example of the generation source analyzing device 100.

FIG. 9 is a drawing showing another configuration example of the generation source analyzing device 100. The generation source analyzing device 100 of the present example receives the weather data from outside and uses the weather data in the extraction of the candidates of the generation sources or the calculation of the contribution proportion. Other configurations are the same as those of the generation source analyzing device 100 in any of the aspects described in FIG. 1 to FIG. 8.

The information processing unit 12 may use the weather data in the process shown in FIG. 6. Also, as another example, in a case of a specified weather condition, the information processing unit 12 may cause the displaying unit 50 to display that the extraction of the candidates of the generation sources is difficult. If it is assumed that the weather condition is that the correlation between the emission of each component in the generation source and the concentration of each component at the measurement point is very small, such as a case of a wind speed being equal to or greater than a predetermined value, a case of a variation frequency of a wind direction being equal to or greater than a fixed frequency, and a case of an amount of rainfall being equal to or greater than a fixed amount, for example, the correlation calculating unit 20 does not calculate the correlation value in the time range in which the time when the weather condition is satisfied is included. Also, the generation source analyzing unit 30 does not extract the candidates of the generation sources at the time when the weather condition is satisfied. According to such an operation, a reliability of the candidates of the generation sources can be improved.

Figure 10:
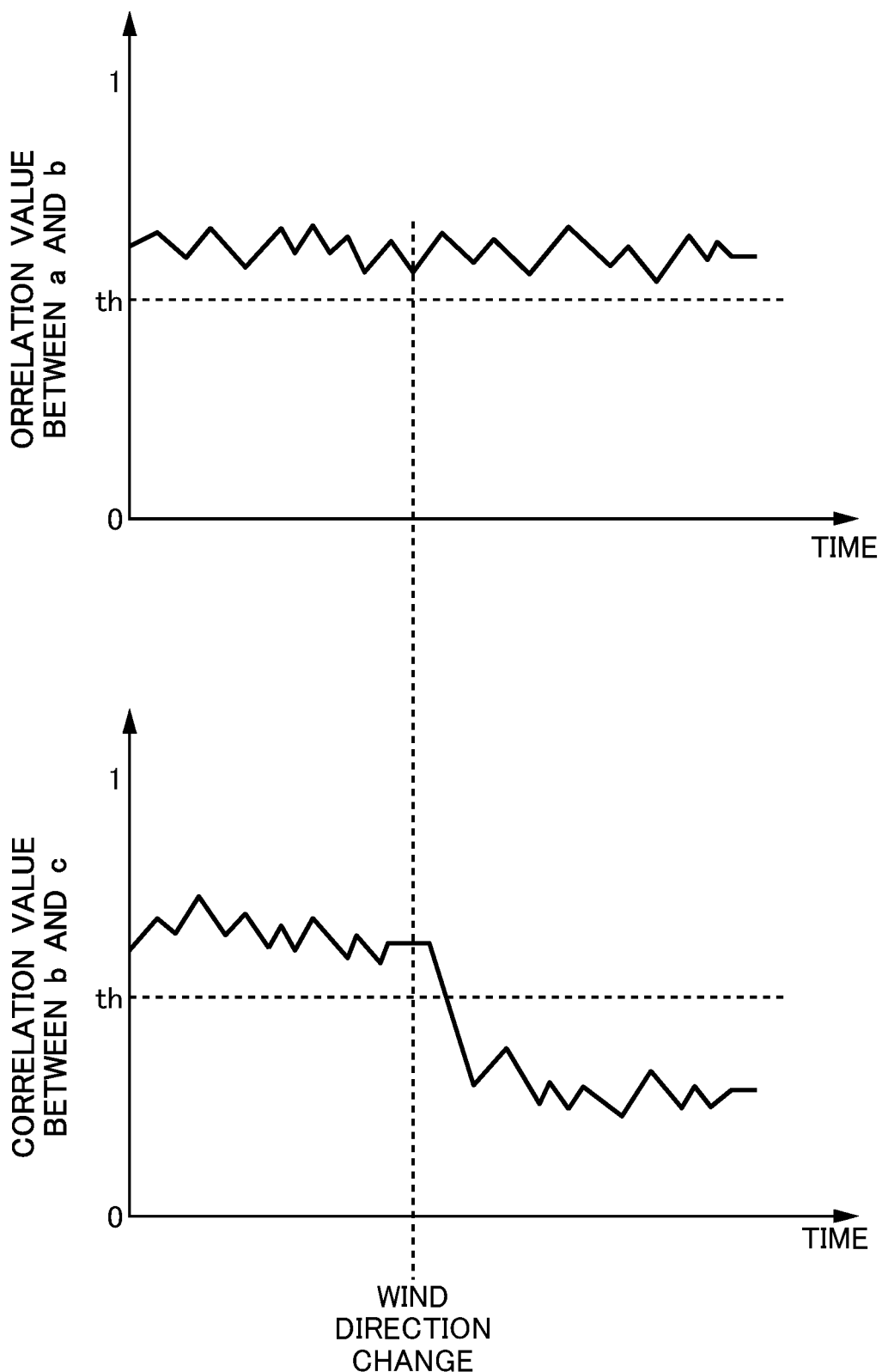
FIG. 10 is a drawing showing another example of an extraction method of the candidates of the generation sources.

FIG. 10 is a drawing showing another example of the extraction method of the candidates of the generation sources. The generation source analyzing unit 30 of the present example extracts the candidates of the generation sources further based on the time-series data of the correlation value. As one example, if a period, in which the correlation value between the components is continuously exceeding the predetermined reference correlation value th, is equal to or greater than a predetermined reference period value, the generation source analyzing unit 30 determines that the generation source which emits the combinations of the components at the same time is located within the predetermined distance from the measurement point.

A percentage that the component emitted from the generation source that is separated a distance equal to or greater than the predetermined distance from the measurement point reaches the measurement point is greatly varied according to the condition such as the wind direction. On the other hand, if the generation source is present in the vicinity of the measurement point, the percentage that the component emitted from the generation source reaches the measurement point is less varied even if the condition such as the wind direction changes. For this reason, if the generation source is present in the vicinity of the measurement point, the correlation value between the components emitted by the generation source at the same time becomes being the high value continuously. If the period, in which the correlation value is continuously exceeding the predetermined reference correlation value th, is equal to or greater than the predetermined reference period value, the generation source analyzing unit 30 may extract the candidates from the generation source which is located within the predetermined distance from the measurement point.

In another example, the generation source analyzing unit 30 may extract the candidates of the generation sources based on the variation of the weather condition such as the wind direction. As one example, if the variation of the correlation value immediately before and after the wind direction is varied is less than a reference variation amount, the generation source analyzing unit 30 extracts, as the candidates, the generation sources which is emitting the combinations of the components corresponding to the correlation value and which is located in a distance from the measurement point within the predetermined distance. The generation source analyzing unit 30 may set, as the condition, that the correlation value is continuously equal to or greater than the reference correlation value th immediately before and after the wind direction is varied.

On the other hand, if the variation of the correlation value immediately before and after the wind direction is varied is larger than the reference variation amount, the generation source analyzing unit 30 may exclude, from the candidates, the generation source which is located in the distance from the measurement point within the predetermined distance even if the generation source is the generation source being emitting the combinations of the components corresponding to the correlation value. The generation source analyzing unit 30 may set, as the condition, that the correlation value crosses the reference correlation value th immediately before and after the wind direction is varied. In this case, during the period in which the correlation value is equal to or greater than the reference correlation value th, it may be determined that the generation source which emits the combinations of the components corresponding to the correlation value in the windward direction exists. Also, during the period in which the correlation value is less than the reference correlation value th, it may be determined that the generation source which emits the combinations of the components corresponding to the correlation value in the windward direction does not exist.

In the example of FIG. 10, because the correlation value between the components a and b is continuously equal to or greater than the reference correlation value th, the generation source analyzing unit 30 determines that the generation source which emits the components a and b is located within the predetermined distance from the measurement point. Because the correlation value between the components b and c is greatly varied at the timing when the wind direction changes, the generation source analyzing unit 30 determines that the generation source which emits the components b and c is not located within the predetermined distance from the measurement point. Also, during a period before the wind direction changes, it is determined that the generation source which emits the components b and c is present in a distance place more than the predetermined distance in the windward direction.

Figure 11:
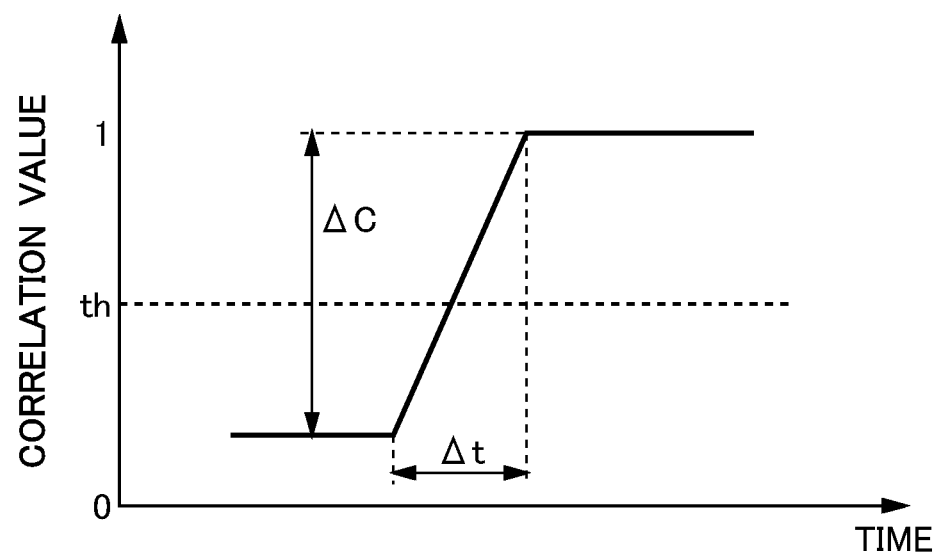
FIG. 11 is a drawing showing another example of the extraction method of the candidates of the generation sources.

FIG. 11 is a drawing showing another example of the extraction method of the candidates of the generation sources. The generation source analyzing unit 30 of the present example extracts the candidates of the generation sources based on the variation of the correlation value. As one example, the generation source analyzing unit 30 calculates the distance range of the generation source extracted as the candidates from the measurement point based on an inclination $\Delta C/\Delta t$ of the variation of the correlation value. The inclination of the variation of the correlation value may be an inclination when the correlation value crosses the reference correlation value th.

For example, the generation source analyzing unit 30 may extract, as the candidates, the generation sources which are located in a close distance from the measurement point as the inclination of the correlation value is larger (steeper). As one example, if any of the generation sources is emitting the primary particles of the component a and the precursor gas of the component b, the timing when the component b reaches the measurement point is delayed compared to the timing when the component a reaches the measurement point. The inclination of the correlation value becomes smaller as the distance to the measurement point becomes larger and the delay time becomes greater.

Figure 12:
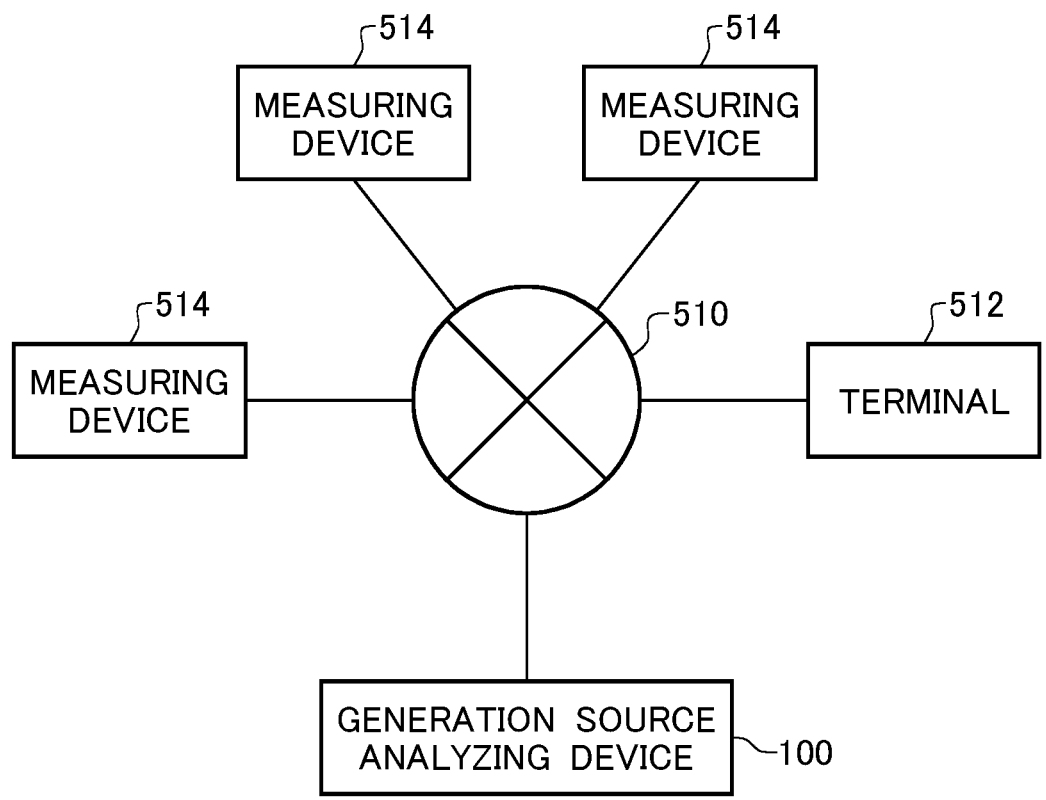
FIG. 12 is a drawing showing a configuration example of a generation source analyzing system 500 according to one embodiment of the present invention.

FIG. 12 is a drawing showing a configuration example of the generation source analyzing system 500 according to one embodiment of the present invention. The generation source analyzing system 500 includes the generation source analyzing device 100. The generation source analyzing device 100 is the generation source analyzing device 100 in any of the aspects described in FIG. 1 to FIG. 11.

The generation source analyzing system 500 includes one or more measuring devices 514. Each of the measuring devices 514 measures the mass concentration of each of the measured object components at predetermined measurement points. The generation source analyzing device 100 receives the location information of the measurement points and the measurement results from the measuring devices 514. The generation source analyzing device 100 extracts the candidates of the generation sources at each of the measurement points.

In the generation source analyzing system 500 of the present example, the generation source analyzing device 100 and each of the measuring devices 514 are connected to each other via a communication network 510. As one example, the communication network 510 is an internet.

In the generation source analyzing system 500 of the present example, one or more terminals 512 and the generation source analyzing device 100 are connected to each other via the communication network 510. The terminals 512 are computer terminals and the like of users. The terminals 512 specify any of the measurement points and time to the generation source analyzing device 100 to request the candidates of the generation sources. The generation source analyzing device 100 notifies the terminals 512 of the candidates of the generation sources extracted relative to the measurement point according to the request.

The terminals 512 may further specify the component. In this case, the generation source analyzing device 100 notifies the terminals 512 of the candidates of the generation sources corresponding to the specified component. According to such a structure, each of the terminals 512 can acquire the information about the candidates of the generation sources at any measurement point and time if accessing to the generation source analyzing device 100, even if each of the terminals 512 does not have the measurement value acquiring unit 10, the information processing unit 12, and the generation source database 40. Also, because the measurement results at a plurality of measurement points can be accumulated in one generation source analyzing device 100, it is possible to perform a generation source analysis by using the measurement results obtained at the plurality of measurement points.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, specifications, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

Various embodiments of the present invention may be described with reference to flowcharts and block diagrams, where the block may represent (i) a step of a process of performing an operation, or (ii) a section of a device having a role of performing an operation. The specified step and section may be implemented by a dedicated circuit, a programmable circuit supplied together with a computer-readable instruction stored on a computer readable medium, and/or a processor supplied together with the computer-readable instruction stored on the computer readable medium. The dedicated circuit may include a digital and/or an analog hardware circuit, and also, the dedicated circuit may include an integrated circuit (IC) and/or a discrete circuit. The programmable circuit may include a reconfigurable hardware circuit that includes a memory element and the like, such as a logical AND, logical OR, logical XOR, logical NAND, logical NOR, and another logical operation, a flip-flop, a register, a field programmable gate array (FPGA), a programmable logic array (PLA).

The computer readable medium may include any tangible device which can store an instruction executed by an appropriate device. As a result, the computer readable medium having an instruction stored thereon becomes to include a product, including the instruction that may be executed so as to make a means for executing an operation specified in the flowcharts or the block diagrams. As examples of the computer readable medium, the followings may be included: an electronic storage medium, a magnetic storage medium, an optical storage medium, an electromagnetic storage medium, a semiconductor storage medium, and the like. As more specific examples of the computer readable medium, the followings may be included: a floppy (registered trademark) disk, a diskette, a hard disk, a random access memory (RAM), a read-only memory (ROM), an erasable programmable read-only memory (EPROM or a flash memory), an electrically erasable programmable read-only memory (EEPROM), a static random access memory (SRAM), a compact disc read-only memory (CD-ROM), a digital versatile disk (DVD), a Blue-ray® disk, a memory stick, an integrated circuit card, and the like.

The computer-readable instruction may include any one of an assembler instruction, an instruction set architecture (ISA) instruction, a machine instruction, a machine-dependent instruction, a microcode, a firmware instruction, a state setting data, or a source code or an object code described in any combination of one or more programming languages including an object-oriented programming language such as Smalltalk, JAVA (registered trademark), and C++, and a conventional procedural programming language such as "C" programming language or a similar programming language.

The computer-readable instruction is provided to a processor or a programmable circuit of a general purpose computer, a special purpose computer, or another programmable data processing apparatus locally or via a local area network (LAN) or a wide area network (WAN) such as an internet, and the computer-readable instruction may be executed so as to make a means for executing an operation specified in the flowcharts or the block diagrams. As examples of the processor, the followings are included: a computer processor, a processing unit, a microprocessor, a digital signal processor, a controller, a micro controller, and the like.

EXPLANATION OF REFERENCES

10 . . . measurement value acquiring unit, 12 . . . information processing unit, 20 . . . correlation calculating unit, 30 . . . generation source analyzing unit, 40 . . . generation source database, 50 . . . displaying unit, 100 . . . generation source analyzing device, 500 . . . generation source analyzing system, 510 . . . communication network 512 . . . terminal, 514 . . . measuring device

What is claimed is:

1. A method of identifying a generation source of a fine particulate matter emission in the atmosphere, comprising:
   generating a plurality of generation source profiles by acquiring an average emission amount of sulfate and an average emission amount of nitrate over a predetermined time period for each of a plurality of generation sources;
   adjusting each of the plurality of generation source profiles for distance to a given measurement point;
   associating a reference sulfate/nitrate correlation value with each of the plurality of generation source profiles;
   periodically measuring, at the given measurement point, a mass concentration of a sulfate component in an emission in the atmosphere, to acquire a time-series plurality of measurement values of mass concentration of the sulfate component in the emission;
   extracting a first variation component from the time-series plurality of measurement values of mass concentration of the sulfate component;
   periodically measuring, at the given measurement point, a mass concentration of a nitrate component in the emission in the atmosphere, to acquire a time-series plurality of measurement values of mass concentration of the nitrate component in the emission;
   extracting a second variation component from the time-series plurality of measurement values of mass concentration of the nitrate component;
   determining a sulfate/nitrate correlation value between the first variation component and the second variation component; and
   notifying a longitude and latitude of at least one likely generation source of the emission from among the plurality of generation sources based on the sulfate/nitrate correlation value exceeding a corresponding reference sulfate/nitrate correlation value associated with a corresponding one of the plurality of generation source profiles.

2. The method of identifying the generation source of the emission according to claim 1, further comprising:
   accessing a generation source database that has recorded an emitted measured object component profile at the measurement point for each of the plurality of possible generation sources.

3. The method of identifying the generation source of the emission according to claim 2, further comprising:
   extracting from the generation source database information indicating a distance between each of the plurality of possible generation sources and the measurement point; and
   adjustment of each of the first time-series plurality of measurement values and each of the second time-series plurality of measurement values according to the distance.

4. The method of identifying the generation source of the emission according to claim 1, further comprising
   determining a contribution proportion of each of the plurality of possible generation sources relative to the measurement value.

5. The method of identifying the generation source of the emission according to claim 1, further comprising, prior to the identifying:
   performing a primary extraction of the plurality of possible generation sources based on the first time-series plurality of measurement values and the second time-series plurality of measurement values; wherein
   the at least one likely generation source of the emission is identified based on the correlation value best matched to one of the primary extracted ones of the plurality of possible generation sources.

6. The method of identifying the generation source of the emission according to claim 1, wherein:
   the at least one likely generation source of the emission is identified based on a length of a period of time in which the correlation value exceeds the reference correlation value.

7. The method of identifying the generation source of the emission according to claim 1, wherein:
   the at least one likely generation source of the emission is identified based on a variation of the correlation value over time.

8. The method of identifying the generation source of the emission according to claim 1, wherein:
   the at least one likely generation source of the emission is identified based on weather data.

9. The method of identifying the generation source of the emission according to claim 1, wherein the determining the correlation value comprises:

extracting a first variation component, which is equal to or higher than a first predetermined frequency of the first time-series plurality of measurement values; and extracting a second variation component, which is equal to or higher than a second predetermined frequency of the second time-series plurality of measurement values.

10. A method of identifying a generation source of a fine particulate matter emission in the atmosphere, comprising:

generating a plurality of generation source profiles by acquiring an average emission amount of sulfate and an average emission amount of black carbon over a predetermined time period for each of a plurality of generation sources;

adjusting each of the plurality of generation source profiles for distance to a given measurement point;

associating a reference sulfate/black carbon correlation value with each of the plurality of generation source profiles;

periodically measuring, at the given measurement point, a mass concentration of a sulfate component in an emission in the atmosphere, to acquire a time-series plurality of measurement values of mass concentration of the sulfate component in the emission;

extracting a first variation component from the time-series plurality of measurement values of mass concentration of the sulfate component;

periodically measuring, at the given measurement point, a mass concentration of a black carbon component in the emission in the atmosphere, to acquire a time-series plurality of measurement values of mass concentration of the black carbon component in the emission;

extracting a second variation component from the time-series plurality of measurement values of mass concentration of the black carbon component;

determining a sulfate/black carbon correlation value between the first variation component and the second variation component; and notifying a longitude and latitude of at least one likely generation source of the emission from among the plurality of generation sources based on the sulfate/black carbon correlation value exceeding a corresponding reference sulfate/black carbon correlation value associated with a corresponding one of the plurality of generation source profiles.

11. A method of identifying a generation source of a fine particulate matter emission in the atmosphere, comprising:

generating a plurality of generation source profiles by acquiring an average emission amount of nitrate and an average emission amount of black carbon over a predetermined time period for each of a plurality of generation sources;

adjusting each of the plurality of generation source profiles for distance to a given measurement point;

associating a reference nitrate/black carbon correlation value with each of the plurality of generation source profiles;

periodically measuring, at the given measurement point, a mass concentration of a nitrate component in an emission in the atmosphere, to acquire a time-series plurality of measurement values of mass concentration of the nitrate component in the emission;

extracting a first variation component from the time-series plurality of measurement values of mass concentration of the nitrate component;

periodically measuring, at the given measurement point, a mass concentration of a black carbon component in the emission in the atmosphere, to acquire a time-series plurality of measurement values of mass concentration of the black carbon component in the emission;

extracting a second variation component from the time-series plurality of measurement values of mass concentration of the black carbon component;

determining a nitrate/black carbon correlation value between the first variation component each and the second variation component; and notifying a longitude and latitude of at least one likely generation source of the emission from among the plurality of generation sources based on the nitrate/black carbon correlation value exceeding a corresponding reference nitrate/black carbon correlation value associated with a corresponding one of the plurality of generation source profiles.

12. A method of identifying a generation source of a fine particulate matter emission in the atmosphere, comprising:

generating a plurality of generation source profiles by acquiring an average emission amount of sulfate and an average emission amount of nitrate over a predetermined time period for each of a plurality of generation sources;

adjusting each of the plurality of generation source profiles for distance to a given measurement point;

associating a reference sulfate/nitrate correlation value with each of the plurality of generation source profiles;

periodically measuring, at the given measurement point, a mass concentration of a sulfate component in an emission in the atmosphere, to acquire a time-series plurality of measurement values of mass concentration of the sulfate component in the emission;

removing a first base component from the time-series plurality of measurement values of mass concentration of the nitrate component;

periodically measuring, at the given measurement point, a mass concentration of a nitrate component in the emission in the atmosphere, to acquire a time-series plurality of measurement values of mass concentration of the nitrate component in the emission;

removing a second base component from the time-series plurality of measurement values of mass concentration of the nitrate component;

determining a sulfate/nitrate correlation value between each of the time-series plurality of measurement values of mass concentration of the sulfate and a corresponding one of the time-series plurality of measurement values of mass concentration of the nitrate; and notifying a longitude and latitude of at least one likely generation source of the emission from among the plurality of generation sources based on the sulfate/nitrate correlation value exceeding a corresponding reference sulfate/nitrate correlation value associated with a corresponding one of the plurality of generation source profiles.

* * * * *